United States Patent
Li et al.

(10) Patent No.: US 9,310,306 B2
(45) Date of Patent: Apr. 12, 2016

(54) APPARATUS FOR USE IN SENSING APPLICATIONS

(75) Inventors: Zhiyong Li, Redwood City, CA (US); Ivan Naumov, Mountain View, CA (US); Farzad Parvaresh, Menlo Park, CA (US)

(73) Assignee: Hewlett-Packard Development Company, L.P., Houston, TX (US)

(*) Notice: Subject to any disclaimer, the term of this patent is extended or adjusted under 35 U.S.C. 154(b) by 61 days.

(21) Appl. No.: 14/006,436

(22) PCT Filed: Mar. 24, 2011

(86) PCT No.: PCT/US2011/029810
§ 371 (c)(1),
(2), (4) Date: Sep. 20, 2013

(87) PCT Pub. No.: WO2012/128773
PCT Pub. Date: Sep. 27, 2012

(65) Prior Publication Data
US 2014/0009758 A1 Jan. 9, 2014

(51) Int. Cl.
*G01J 3/44* (2006.01)
*G01N 21/65* (2006.01)
*B05D 3/00* (2006.01)

(52) U.S. Cl.
CPC ............... *G01N 21/65* (2013.01); *B05D 3/007* (2013.01); *G01N 21/658* (2013.01)

(58) Field of Classification Search
CPC ............................ G01N 21/658; G01N 21/65
See application file for complete search history.

(56) References Cited

U.S. PATENT DOCUMENTS

| | | | |
|---|---|---|---|
| 6,756,795 B2 | 6/2004 | Hunt et al. | |
| 7,212,284 B2 * | 5/2007 | Deng et al | 356/301 |
| 7,667,238 B2 | 2/2010 | Erchak | |
| 7,833,842 B2 | 11/2010 | Williams | |
| 7,884,930 B2 * | 2/2011 | Kirby et al. | 356/301 |
| 8,767,202 B2 * | 7/2014 | Schmidt et al. | 356/301 |
| 9,013,689 B2 * | 4/2015 | Reinhard et al. | 356/301 |
| 2006/0231381 A1 | 10/2006 | Jensen et al. | |
| 2008/0017845 A1 | 1/2008 | Drndic et al. | |
| 2008/0024776 A1 | 1/2008 | Bratkovski et al. | |

(Continued)

FOREIGN PATENT DOCUMENTS

| | | |
|---|---|---|
| EP | 2058908 | 5/2009 |
| EP | 2128595 A1 | 12/2009 |

(Continued)

OTHER PUBLICATIONS

Gopinath, et al. "Deterministic aperiodic arrays of metal nanoparticles for surface-enhanced Raman scattering (SERS)." Optics Express 17.5 (Feb. 25, 2009): pp. 3741-3753.*

(Continued)

*Primary Examiner* — Kara E Geisel
*Assistant Examiner* — Shawn Decenzo
(74) *Attorney, Agent, or Firm* — Mannava & Kang, P.C.

(57) ABSTRACT

An apparatus for use in sensing applications includes a substrate and a plurality of clusters arranged in an aperiodic configuration on the substrate, wherein each of the plurality of clusters is formed of a plurality of Raman-active material nano-particles, and wherein each of the Raman-active material nano-particles is positioned in a substantially ordered configuration with respect to each other in each of the respective plurality of clusters.

8 Claims, 6 Drawing Sheets

(56) References Cited

U.S. PATENT DOCUMENTS

| | | | |
|---|---|---|---|
| 2008/0174775 | A1 | 7/2008 | Moskovitz et al. |
| 2008/0311028 | A1 | 12/2008 | Stanbery |
| 2009/0261815 | A1 | 10/2009 | Cairns et al. |
| 2011/0001118 | A1 | 1/2011 | Bhupendra |
| 2011/0030792 | A1 | 2/2011 | Miguez |
| 2011/0053794 | A1 | 3/2011 | Zhang |
| 2012/0013903 | A1* | 1/2012 | Kuo et al. ............... 356/301 |
| 2012/0212732 | A1 | 8/2012 | Santori et al. |
| 2013/0040862 | A1* | 2/2013 | Li et al. .................. 506/20 |

FOREIGN PATENT DOCUMENTS

| | | |
|---|---|---|
| TW | 200407536 A | 5/2004 |
| WO | WO-2008028130 A1 | 3/2008 |
| WO | WO-2010081088 A1 | 7/2010 |
| WO | WO-2010088585 | 8/2010 |
| WO | WO-2010126640 | 11/2010 |
| WO | WO-2011133143 | 10/2011 |

OTHER PUBLICATIONS

Hu et al. "Gold nanofingers for molecule trapping and detection." Journal of the American Chemical Society 132.37 (2010): 12820-12822.*

Liang, Y. N., et al. "Micro-ink-jetting of silver nanoparticles on low temperature cofired ceramic substrates for drop-on-demand metallization." Journal of Vacuum Science & Technology B 27.3 (Pub. Year: 2009): pp. 1431-1436.*

Baldwin, Jean, et al., "Integrated Optics Evanescent Wave Surface Enhanced Raman Scattering (IO-EWSERS) of Mercaptopyridines on a Planar Optical Chemical Bench: Binding of Hydrogen and Copper Ion", Langmuir, 1996, vol. 12, pp. 6389-6398.

Giglmayr, Josef, "Nano-Finger Electrodes for the Electro-Optical Generation and Tuning of Gratings at Several Wavelengths",<http://www.ipme.ru/ipme/conf/NN2003/NN2003_Abstracts.pdf> Pub Date: Aug. 30, 2003—Sep. 6, 2003.

Gopinath, Ashwin, et al., "Deterministic Aperiodic Arrays of Metal Nanoparticles for Surface-enhanced Raman Scattering (SERS)", <http://www.bio-page.org/boriskina/Boriskina_OE2009.pdf>, Pub Date: Mar. 2, 2009; vol. 17.

International Search Report, Korean IPO, Sep. 29, 2011, PCT Patent Application No. PCT/US2011/029810.

Krishnamoorthy, Sivashankar, et al., "Combining Micelle Self-assembly with Nanostencil Lithography to Create Periodic/aperiodic Micro-/nanopatterns on Surfaces", <http://onlinelibrary.wiley.com/doi/10.1002/adma.200702478/abstract>, Pub Date: Jul. 30, 2008.

Qiu, T. et al., 'Surface-enhanced Raman characteristics of Ag cap aggregates on silicon nanowire array' Nanotechnology 17 5769 doi: 10.1088/0957-4484/17/23/ 010, Nov. 10, 2006.

* cited by examiner

APPARATUS FOR USE IN SENSING APPLICATIONS

STATEMENT REGARDING FEDERALLY SPONSORED RESEARCH OR DEVELOPMENT

This invention has been made with government support awarded by Defense Advanced Research Projects Agency. The government has certain rights in the invention.

CROSS-REFERENCE TO RELATED APPLICATION

The present application contains some common subject matter with PCT Application No. PCT/US/2010/031790, filed on Apr. 20, 2010, and U.S. patent application Ser. No. 13/029,915, filed on Feb. 17, 2011, the disclosures of which are hereby incorporated by reference in their entireties.

BACKGROUND

Detection and identification or at least classification of unknown substances has long been of great interest and has taken on even greater significance in recent years. Among advanced methodologies that hold a promise for precision detection and identification are various forms of spectroscopy, especially those that employ Raman scattering. Spectroscopy may be used to analyze, characterize and even identify a substance or material using one or both of an absorption spectrum and an emission spectrum that results when the material is illuminated by a form of electromagnetic radiation (for instance, visible light). The absorption and emission spectra produced by illuminating the material determine a spectral 'fingerprint' of the material. In general, the spectral fingerprint is characteristic of the particular material or its constituent elements facilitating identification of the material. Among the most powerful of optical emission spectroscopy techniques are those based on Raman scattering.

Raman scattering optical spectroscopy employs an emission spectrum or spectral components thereof produced by inelastic scattering of photons by an internal structure of the material being illuminated. These spectral components contained in a response signal (for instance, a Raman signal) may facilitate determination of the material characteristics of an analyte species including identification of the analyte.

Unfortunately, the signal produced by Raman scattering is extremely weak in many instances compared to elastic or Rayleigh scattering from an analyte species. The Raman signal level or strength may be significantly enhanced by using a Raman-active material (for instance, Raman-active surface), however. For instance, the Raman scattered light generated by a compound (or ion) adsorbed on or within a few nanometers of a structured metal surface can be $10^3$-$10^{12}$ times greater than the Raman scattered light generated by the same compound in solution or in the gas phase. This process of analyzing a compound is called surface-enhanced Raman spectroscopy ("SERS"). In recent years, SERS has emerged as a routine and powerful tool for investigating molecular structures and characterizing interfacial and thin-film systems, and even enables single-molecule detection.

Most SERS systems only enhance the electro-magnetic field at certain hot spots. While this can be very desirable, in many cases, the analytes are spread evenly on a SERS substrate, such as by simple adsorption. However, only a small fraction of the analytes actually populates the hot spots. In addition, conventional SERS systems employ periodic arrays of the Raman-active materials, which may cause a grating effect, such that certain angles of light propagation often yield optimal signal emission performance, while other angles often yield poor signal emission performance.

BRIEF DESCRIPTION OF THE DRAWINGS

Features of the present disclosure are illustrated by way of example and not limited in the following figure(s), in which like numerals indicate like elements, in which.

DETAILED DESCRIPTION

For simplicity and illustrative purposes, the present disclosure is described by referring mainly to an example thereof. In the following description, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure.

Throughout the present disclosure, the terms "a" and "an" are intended to denote at least one of a particular element. As used herein, the term "includes" means includes but not limited to, the term "including" means including but not limited to. The term "based on" means based at least in part on. In addition, the term "light" refers to electromagnetic radiation with wavelengths in the visible and non-visible portions of the electromagnetic spectrum, including infrared and ultraviolet portions of the electromagnetic spectrum.

Disclosed herein are an apparatus for use in sensing applications and a method for fabricating a sensing apparatus. The apparatus includes a plurality of clusters arranged in an aperiodic configuration on a substrate. The clusters are each formed of a plurality of Raman-active material nano-particle collections, in which the nano-particle collections are positioned in a substantially ordered configuration with respect to each other in each of the respective plurality of clusters. According to a particular example, each of the clusters includes five metallic nano-particle collections and the collections are arranged in a pentamer configuration. In addition, the clusters are formed on top of nano-fingers that have been formed into a predetermined configuration and the tips of which have been brought into close contact with each other. The nano-fingers thus provide surfaces upon which the clusters of the Raman-active material nano-particles may be deposited to form the desired patterns of collections in each of the clusters.

Through implementation of the apparatus and method disclosed herein, a plurality of hot spots for enhanced fluorescence, enhanced luminescence, etc., may be created on various types of substrates. In addition, the hot spots may be created aperiodically on the substrate, such that, the hot spots are not subject to the grating effect that occurs with periodic configurations of active materials. As such, the apparatus and method disclosed herein may eliminate possible angle-dependent signal emission performance. In addition, the uniformity of the cluster distribution may potentially be increased in any direction at which analyte is observed on the apparatus.

Figure 1A:
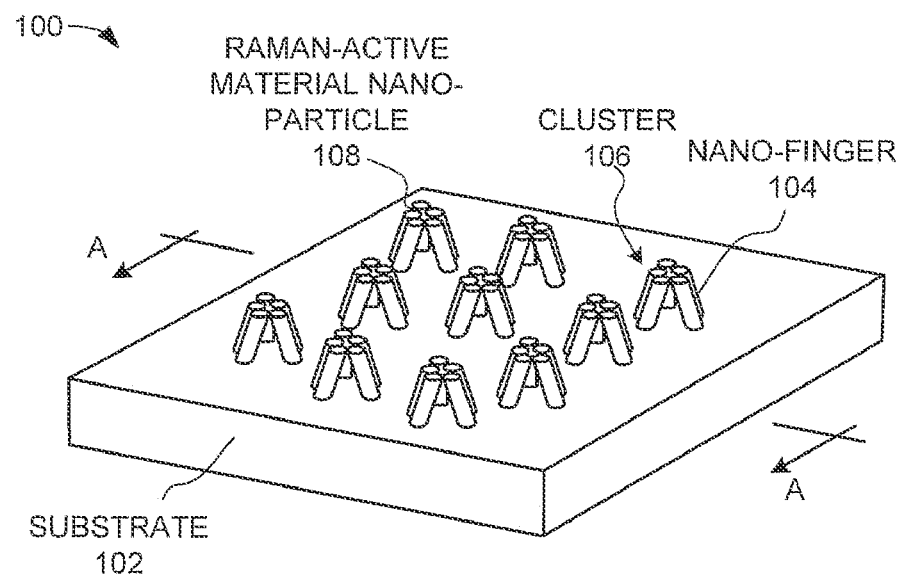
FIG. 1A shows an isometric view of an apparatus for use in sensing applications, according to an example of the present disclosure.

FIG. 1A shows an isometric view of an apparatus 100 for use in sensing applications, according to an example. It should be understood that the apparatus 100 depicted in FIG. 1A may include additional components and that some of the components described herein may be removed and/or modified without departing from a scope of the apparatus 100. It should also be understood that the components depicted in FIG. 1A are not drawn to scale and thus, the components may have different relative sizes with respect to each other than as shown therein.

The apparatus 100 is operable to be used in sensing applications, for instance, to detect a molecule in an analyte sample with a relatively high level of sensitivity. According to various examples, the apparatus 100 may be employed in surface enhanced Raman spectroscopy (SERS), enhanced fluorescence, enhanced luminescence, etc., types of applications.

The apparatus 100 is depicted as including a substrate 102 supporting a plurality of nano-fingers 104. The substrate 102 generally comprises any reasonably suitable material to support the nano-fingers 104, such as, glass, plastic, polymer, metal, etc. The nano-fingers 104 may be attached to the surface of the substrate 102 through any suitable attachment mechanism. For instance, the nano-fingers 104 may be grown directly on the optical substrate 102 surface through use of various suitable nano-structure growing techniques. As another example, the nano-fingers 104 may be integrally formed with the substrate 102. In this example, for instance, a portion of the material from which the substrate 102 is fabricated may be etched or otherwise processed to form the nano-fingers 104. In a further example, a separate layer of material may be adhered to the substrate 102 surface and the separate layer of material may be etched or otherwise processed to form the nano-fingers 104.

The nano-fingers 104 are formed of a relatively flexible material to enable the nano-fingers 104 to be laterally bendable, for instance, to enable free ends of the nano-fingers 104 to move toward each other, as discussed in greater detail herein below. Examples of suitable materials for the nano-fingers 104 include polymer materials, such as, polydimethylsiloxane (PDMS) elastomer, polyimide, polyethylene, polypropelene, etc., or any combination of thereof, metallic materials, such as, gold, silver, aluminum, etc., semiconductor materials, etc., and combinations thereof. In various examples, the nano fingers 104 may be fabricated through a nanoimprinting or embossing process in which a template of relatively rigid pillars is employed in a multi-step imprinting process on a polymer matrix to form the nano-fingers 104. Various other processes, such as, etching, and various techniques used in the fabrication of micro-electromechanical systems (MEMS) and nano-electromechanical systems (NEMS) may also be used to fabricate the nano-fingers 104.

A nano-finger 104 may be defined as an elongated, nanoscale structure having a length (or height) that exceeds by more than several times a nanoscale cross sectional dimension (for instance, width) taken in a plane perpendicular to the length (for instance, length>3×width). In general, the length is much greater than the width or cross sectional dimension to facilitate bending of the nano-finger 104 laterally onto one or more neighboring nano-fingers 104. In some examples, the length exceeds the cross sectional dimension (or width) by more than a factor of about 5 or 10. For example, the width may be about 100 nanometers (nm) and the height may be about 500 nm. In another example, the width at the base of the nano-finger 104 may range between about 20 nm and about 300 nm and the length may be more than about 1 micrometer (µm). In other examples, the nano-finger 104 is sized based upon the types of materials used to form the nano-finger 104. Thus, for instance, the more rigid the material(s) used to form the nano-finger 104, the less the width of the nano-finger 104 may be to enable the nano-finger 104 to be laterally collapsible. In further examples, the nano-finger 104 may form ridges in which two of three dimensions (for instance length and height) exceed by more than several times a nanoscale cross sectional dimension (for instance, width). According to particular examples, the heights of the nano-fingers 104 may be in the range of about 50 nm to 2 µm and their diameter may be in the range of about 10 nm to 1 µm. In addition, the nano-fingers 104 may equivalently be references as nanopoles or nanopillars without departing from a scope of the apparatus 100.

As shown in FIG. 1A, the nano-fingers 104 are arranged in respective groups or clusters 106 on the substrate 102. The clusters 106 are also used herein to define Raman-active material nano-particles 108. As discussed in greater detail herein below, the nano-fingers 104 may be arranged in substantially ordered configurations within each cluster 106. However, the clusters 106 are arranged in an aperiodic configuration on the substrate 102. In other words, the clusters 106 are arranged such that there is no periodicity in the x and y dimensions. An example of a suitable aperiodic configuration for the clusters 106 is a penrose configuration.

In any regard, and as discussed in greater detail herein below, the nano-fingers 104 in each of the clusters 106 are arranged with respect to each other such that the free ends of at least two neighboring nano-fingers 104 are able to touch each other when the nano-fingers 104 are in a bent condition. By way of particular example, the neighboring nano-fingers 104 are positioned less than about 100 nanometers apart from each other. Each of the clusters 106 has been depicted as including five nano-fingers 104, in which the clusters 106 have five-fold symmetry or a quasi-crystal pattern. It should, however, be understood that each of the clusters 106 may include a lesser or greater number of nano-fingers 104 in symmetrical or asymmetrical arrangement and that different clusters 106 may include different numbers of nano-fingers 104 without departing from a scope of the apparatus 100.

The nano-fingers 104 have been depicted in FIG. 1A as having substantially cylindrical cross-sections. It should, however, be understood that the nano-fingers 104 may have other shaped cross-sections, such as, for instance, rectangular, square, triangular, etc. In addition, or alternatively, the nano-fingers 104 may be formed with one or more features, such as, notches, bulges, etc., to substantially cause the nano-fingers 104 to be inclined to bend in a particular direction. Thus, for instance, two or more adjacent nano-fingers 104 may include the one or more features to increase the likelihood of the free ends of these nano-fingers 104 to bend toward each other.

The tips of the nano-fingers 104 are also depicted as including Raman-active material nano-particles 108. Examples of the Raman-active material nano-particles 108 are discussed in greater detail with respect to FIG. 1B, which shows a cross-sectional view along a line A-A, shown in FIG. 1A, of the apparatus 100, in accordance with an example. In addition, a free end of a nano-finger 104 is magnified in an enlargement 120, which reveals that the Raman-active material nano-particles 108 may be formed of a collection of atoms or atom clusters 110. In addition, although the Raman-active material nano-particle 108 has been depicted as having a rough surface, the Raman-active material nano-particle 108 may comprise a continuous layer of the Raman-active material and may have a relatively smooth surface. Moreover, the Raman-active material nano-particles 108 may have various other shapes than those depicted in FIG. 1B. For instance, the Raman-active material nano-particles 108 may have rounded edges, extend beyond an outer perimeter of the nano-fingers 104, etc.

According to an example, the Raman-active material nano-particles 108 comprise a metal, such as, gold, silver, copper, platinum, aluminum, etc., or a combination of these metals in the form of alloys, or other suitable material that is able to support surface plasmons for field enhancement for Raman scattering. In addition, the Raman-active material nano-particles 108 may be multilayer structures, for example, 10 to 100 nm silver layer with 1 to 50 nm gold over-coating, or vice versa. In addition, or alternatively, the Raman-active material nano-particles 108 may be further coated with a thin dielectric layer, or functional coating, such as ALD-grown silicon oxide or aluminum oxide, titanium oxide, etc. By definition herein, a Raman-active material is a material that supports surface plasmons and facilitates Raman scattering from an analyte adsorbed on or near a surface layer of the material during Raman spectroscopy.

The other nano-fingers 104 may also include the Raman-active material nano-particles 108 as represented by the shaded rectangles on the tops or free ends of the nano-fingers 104. Although the enlargement 120 depicts the collection of atoms or atom clusters 110 as covering the entire tip of the nano-finger 104, it should be understood that examples of the apparatus 100 may be implemented with gaps between some of the atoms or atom clusters 110. It should also be noted that examples of the apparatus 100 are not limited to atoms or atom clusters 110 disposed over just the tips of the nano-scale protrusions 104. In other examples, the atoms or atom clusters 110 may be disposed over part of or nearly the entire surface of the nano-fingers 104. In any regard, the atoms or atom clusters 110 may be deposited onto at least the free ends of the nano-fingers 104 through, for instance, physical vapor deposition (PVD), chemical vapor deposition (CVD), sputtering, etc., of metallic material, or self-assembly of pre-synthesized nano-particles. By way of example, the angle at which the atoms or atom clusters 110 are deposited onto the free second ends of the nano-fingers 104 may be controlled to thereby substantially control the deposition of the atoms or atom clusters 110.

In some examples, a surface of the nano-fingers 104 and/or the Raman-active material nano-particles 108 may be functionalized to facilitate adsorption of the analyte. For example, the tips or free ends of the nano-fingers 104 in a vicinity thereof (not illustrated) may be functionalized with a binding group to facilitate binding with a specific target analyte species. The functionalized surface (that is, either a surface of the nano-finger 104 itself and/or the Raman-active material nano-particles 108 may provide a surface to which a particular class of analytes is attracted and may bond or be preferentially adsorbed. The functionalized surface may selectively bond with protein, DNA or RNA, for example.

Figure 1B:
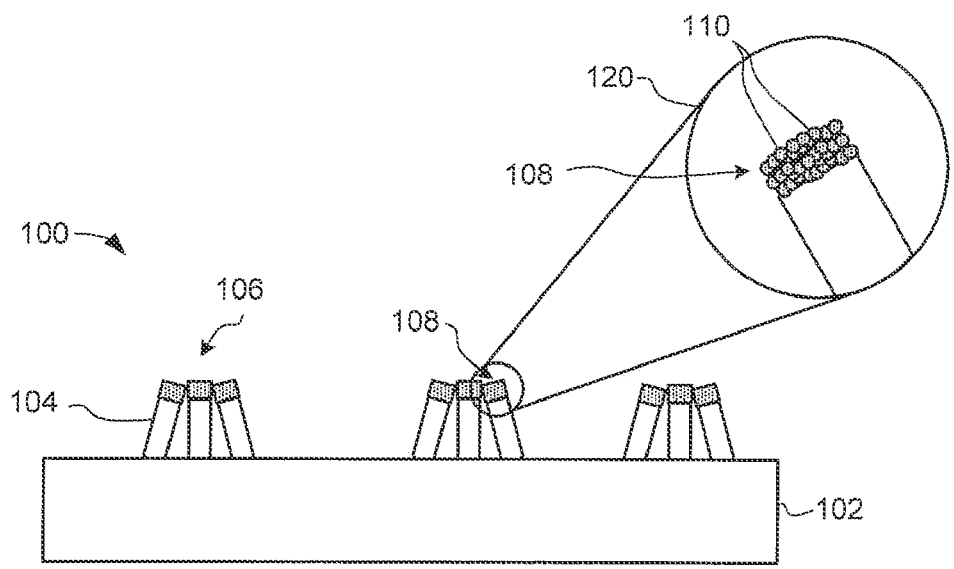
FIG. 1B show a cross-sectional view along a line A-A, shown in FIG. 1A of the apparatus, according to an example of the present disclosure.

Although the nano-fingers 104 have been depicted in FIGS. 1A-1B as each extending vertically and at the same heights with respect to each other, it should be understood that some or all of the nano-fingers 104 may extend at various angles and heights with respect to each other. The differences in angles and/or heights between the nano-fingers 104 may be based upon, for instance, differences arising from manufacturing or growth variances existent in the fabrication of the nano-fingers 104 and the deposition of the nano-particles 110 on the nano-fingers 104, etc.

Although not shown in the figures, the nano-fingers 104 may initially be in a first position, in which their free ends are in a substantially spaced arrangement with respect to each other. The gaps between the free ends may be of sufficiently large size to enable a liquid to be supplied in the gaps. In addition, the gaps may be of sufficiently small size to enable the free ends of the nano-fingers 104 in each of the clusters 106 to move toward each other as the liquid evaporates, through, for instance, capillary forces applied on the free ends as the liquid dries. According to an example, an analyte to be tested using the apparatus 100 is included in the liquid to thus enable molecules from the analyte to be trapped between the tips (and/or the Raman-active material nano-particles 108). Other non-limiting examples, such as e-beam, ion-beam, magnetic, mechanical force, thermal effect, or electric charge effect, may also be utilized to cause the ends of the nano-fingers 104 to move toward each other. In addition, the tips of the nano-fingers 104, and/or the Raman-active material nano-particles 108, in each of the clusters 106 may contact each other and remain in contact with each other through van der Waals interactions between those elements.

Figure 1C:
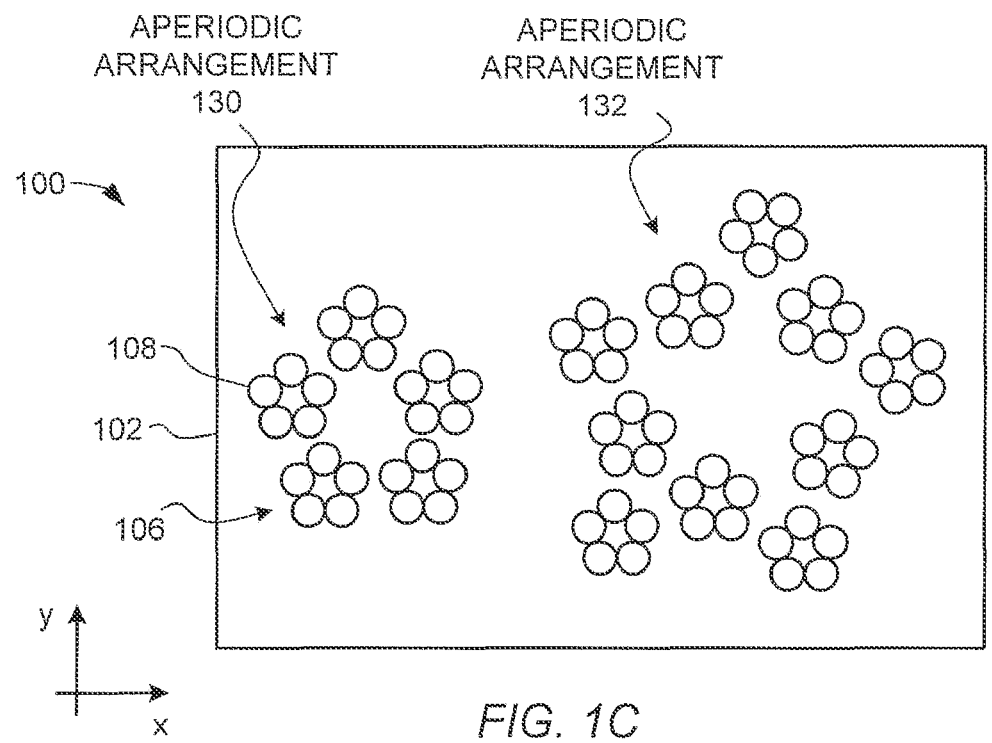
FIGS. 1C and 1D respectively show top views of the apparatus depicted in FIGS. 1A and 1B, according to examples of the present disclosure.

Turning now to FIG. 1C, there is shown a top view of the apparatus 100, according to an example. Shown in FIG. 1C are two aperiodic arrangements 130 and 132 of the clusters 106 of Raman-active material nano-particles 108. Although not shown, the nano-fingers 104 supporting the Raman-active material nano-particles 108 may also be included in the apparatus 100. Alternatively, each of the circles may merely represent a Raman-active material nano-particle 108 that has been removed from their respective nano-finger 104 tips.

Figure 1D:
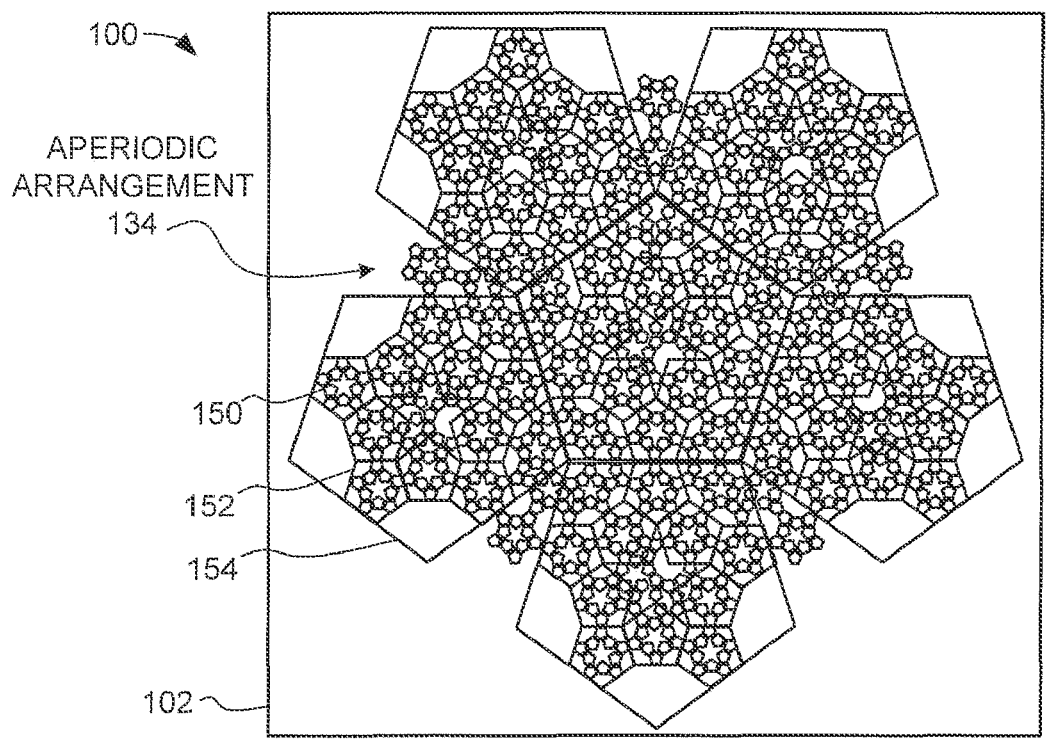

As shown by the aperiodic arrangements 130 and 132, the clusters 106 may be arranged in various configurations with respect to each other, such that, there is no periodicity in the x and y dimensions. In other words, if the patterns of clusters 106 are shifted in the x or y directions, the shifted patterns may not be overlaid with the original pattern. The clusters 106 may also be arranged in relatively more complex aperiodic arrangements that substantially maximize coverage of the clusters 106 on the substrate 102 without forming a periodic configuration. An example of a relatively more complex aperiodic arrangement 134 of clusters 106 is depicted in FIG. 1D. It should, however, be understood that the clusters 106 may be arranged in various other relatively complex aperiodic arrangements. In addition, it should be understood that the clusters 106 may be arranged in a predetermined aperiodic configuration that substantially avoids overlapping of the plurality of clusters on each other.

In FIG. 1D, each of the smallest pentagons 150 represents a cluster 106 of Raman-active material nano-particles 108. Each of the smallest pentagons 150 may represent one of the clusters 106 depicted in FIG. 1C and may thus contain five Raman-active material nano-particles 108 arranged in a pentamer configuration with respect to each other. The larger pentagons 152 have been depicted in FIG. 1D to show a general pattern of nine of the smallest pentagons 150 arranged in a particular pattern. Likewise, the largest pentagons 154 have been depicted to show a general pattern of nine of the larger pentagons 152 arranged in a particular pattern. These patterns may be repeated to cover a desired amount of space on a substrate 102. Although not shown, nano-fingers 104 supporting the Raman-active material nano-particles 108 may also be included in the apparatus 100 depicted in FIG. 1D. Alternatively, each of the circles may merely represent a Raman-active material nano-particle 108 that has been removed from their respective nano-finger 104 tips.

Figure 2A:
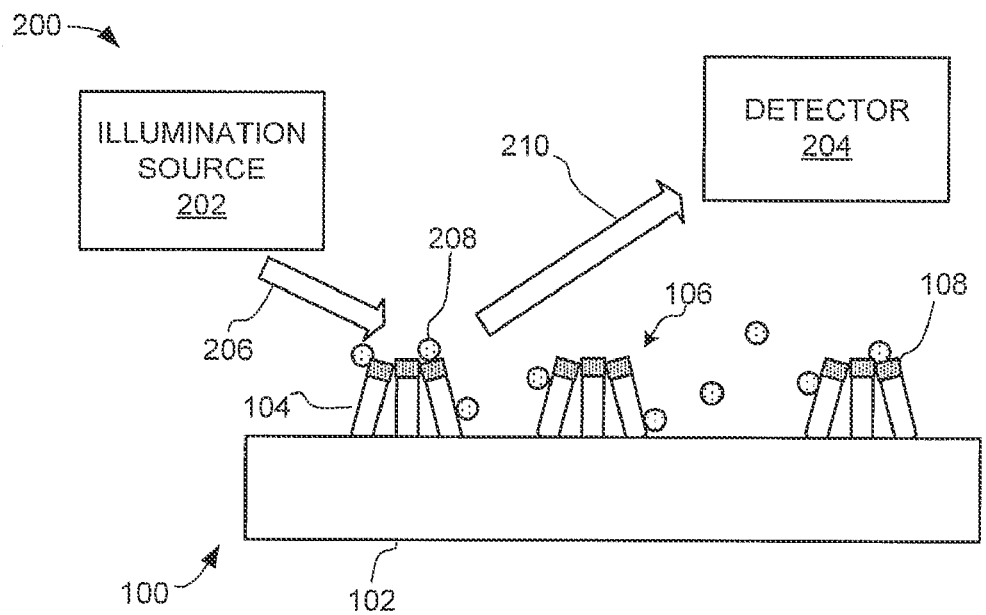
FIGS. 2A and 2B respectively show block diagrams of apparatuses for use in sensing applications, according to examples of the present disclosure.
Figure 2B:
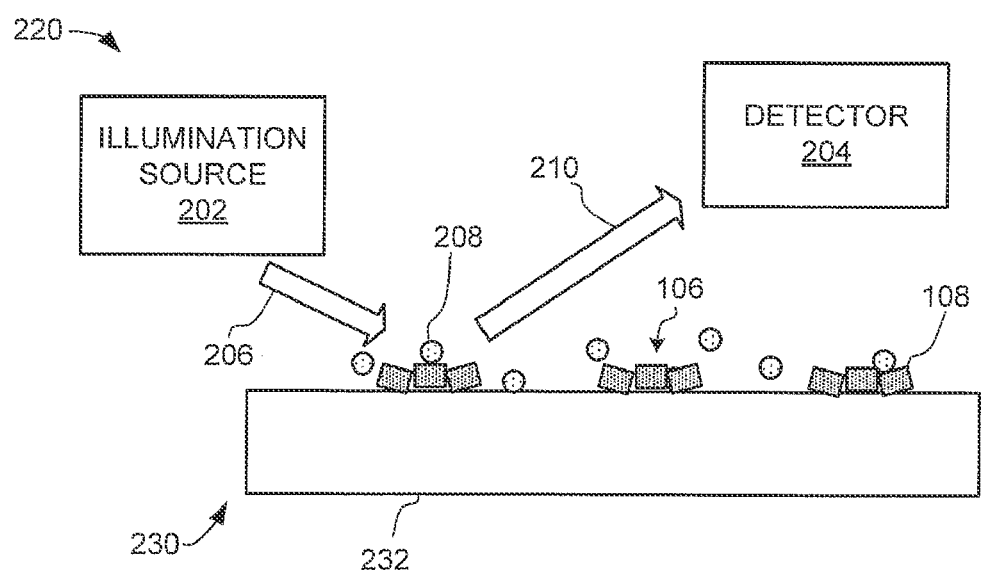

With reference now to FIGS. 2A and 2B, there are respectively shown block diagrams of apparatuses 200, 220 for use in sensing applications, according to two examples. It should be understood that the apparatuses 200, 220 may include additional components and that some of the components described herein may be removed and/or modified without departing from the scopes of the apparatuses 200, 220. It should also be understood that the components depicted in the apparatuses 200, 220 are not drawn to scale and thus, the components may have different relative sizes with respect to each other than as shown therein.

As shown in FIG. 2A, the apparatus 200 includes the apparatus 100 depicted in FIGS. 1A-1D, an illumination source 202 and a detector 204. In addition, similarly to the view depicted in FIG. 1B, the nano-fingers 104 are illustrated as being in the second position, in which, the free ends of the nano-fingers 104 in each of the clusters 106 are in contact with each other. In FIG. 2B, the apparatus 220 is depicted as including a different sensing application apparatus 230 from the apparatus 100, but includes the illumination source 202 and the detector 204. More particularly, the apparatus 220 in FIG. 2B is depicted as including a substrate 232 that may differ from the substrate 102 depicted in FIG. 2A. In addition, in the apparatus 230, the clusters 106 of Raman-active material nano-particles 108 are depicted as being positioned directly on the substrate 232. The clusters 106 of Raman-active material nano-particles 108 may therefore have been removed from the nano-fingers 104 through any of a variety of processes. For instance, the clusters 106 may simply have been attached to the substrate 232 and removed from the nano-fingers 104. In another example, the nano fingers 104 may have been dissolved or otherwise removed, leaving the cluster 106, which may then have been positioned on the substrate 232. In a yet further example, the clusters 106 may have been deposited onto the substrate 232 through use of a fluid jetting device.

In both apparatuses 200 and 220, an analyte molecule 208 to be tested is depicted as being positioned on a Raman-active material nano-particle 108. Additional analyte molecules 208 have been depicted as being present around the clusters 106. The analyte molecules 208 may be introduced onto the apparatus 100, 230 prior to the tips of the nano-fingers 104 being drawn together or after the tips have been drawn together.

The illumination source 202 is depicted as emitting electromagnetic radiation, as represented by the arrow 206, which may comprise, for instance, light. By way of example, the illumination source 202 may comprise a laser that illuminates the Raman-active material nano-particles 108 and the analyte molecules 208. Illumination of the Raman-active material nano-particles 108 causes hot spots of relatively large electric field strength to occur. The hot spots are increased at the locations where the Raman-active material nano-particles 108 contact each other. The electric fields generated at the contact locations between the Raman-active material nano-particles 108 generally enhance the rate at which Raman light is scattered by an analyte molecule 208 positioned at or near the contact locations. The Raman scattered light, which is represented by the arrow 210, is shifted in frequency by an amount that is characteristic of particular vibrational modes of the analyte molecule 208. The detector 204 is to collect the Raman scattered light 210 and spectral analysis may be performed on the Raman scattered light 210 to identify the analyte molecule 208 or to detect that the analyte molecule 208 has been illuminated.

The Raman-active material nano-particles 108 located near or adjacent to the analyte molecule(s) 208 may enhance the production of Raman scattered light 210 from the analyte molecule(s) 208 by concentrating or otherwise enhancing an electromagnetic field in a vicinity of the analyte molecule(s) 208. As also discussed above, the contacting of two or more of the Raman-active material nano-particles 108 with each other may trap the analyte molecule(s) 208, which may substantially increase the likelihood that the analyte molecule(s) 208 will be positioned near or in contact with some Raman-active material nano-particles 108 and thus be positioned within a hot spot. In this regard, the likelihood that an analyte molecule(s) 208 will produce sufficiently strong Raman scattered light 210 to be detected by the detector 204 will thus also be increased.

Although the Raman scattered light 210 has been depicted as being directed toward the detector 204, the Raman scattered light 210 is emitted in multiple directions. In this regard, some of the Raman scattered light 210 may be directed into the substrate 102, 232, which may comprise an optical waveguide. More particularly, for instance, Raman scattered light 210 may be generated in the substrate 102, 232 as a result of the analyte molecule 208 coupling to the evanescent field of a waveguide mode. In these instances, the detector 204 may be positioned to detect the waves generated in the substrate 102 from the Raman scattered light 210. In any regard, the detector 204 may include a filter to filter out light originating from the illumination source 202, for instance, through use of a grating-based monochrometer or interference filters. Various examples in which the substrate 102, 232 comprises an optical waveguide are described in the Ser. No. 13/029,915 application for patent.

The detector 204 is generally to convert the Raman scattered light 210 emitted from the analyte molecule(s) 208 into electrical signals that may be processed to identify, for instance, the analyte molecule 208 type. In some examples, the detector 204 is to output the electrical signals to other components (not shown) configured to process the electrical signals. In other examples, the detector 204 is equipped with processing capabilities to identify the analyte molecule 208 type.

According to an example, the apparatus 200 comprises a system that is integrated on a single chip. For example, the output of the substrate 102, 232 may be connected to an arrayed waveguide grating (AWG filter). The substrate 102, 232 may also be directly coupled to optical fibers in the apparatus 200 through which the illumination light 206 may be supplied and through which the Raman scattered light 210 may be outputted. In this example, the apparatus 200 provides a relatively more compact solution than coupling free-space signals to fibers. Additionally, the apparatus 200 may be implemented efficiently for a relatively large sensing area for which the free-space signals are substantially more complex and/or expensive to implement. The substrate 102 in the apparatus 200 may also be directly coupled to optical fibers in particular instances to form compact field sensors. In this instance, the illumination source 202, for instance an excitation laser, and the detector 204, for instance spectral analysis equipment, may then be housed in a remote location.

Figure 3:
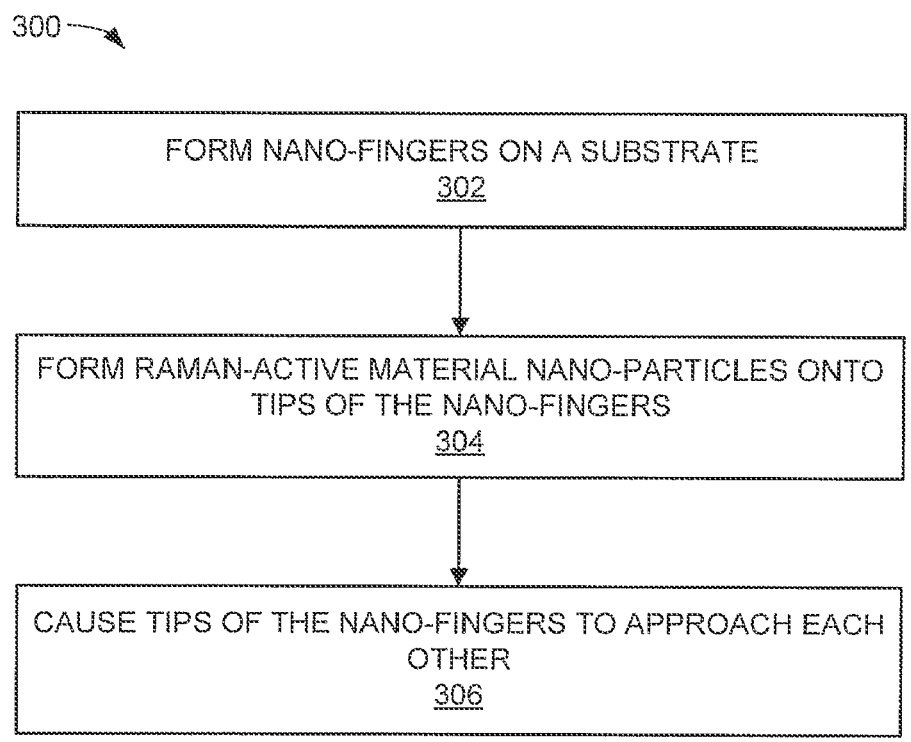
FIGS. 3 and 4 respectively show flow diagrams of methods for fabricating a sensing apparatus, according to examples of the present disclosure.

Turning now to FIG. 3, there is shown a flow diagram of a method 300 for fabricating a sensing apparatus, according to an example. It should be understood that the method 300 may include additional processes and that some of the processes described herein may be removed and/or modified without departing from a scope of the method 300. In addition, although particular reference is made herein to the apparatus 100 in implementing the method 300, it should be understood that the method 300 may be implemented through use of a differently configured apparatus without departing from a scope of the method 300.

At block 302, a plurality of nano-fingers 104 are formed on a substrate 102 in a predetermined arrangement, in which the nano-fingers 104 are arranged in respective ordered dusters 106, and in which the ordered dusters 106 are arranged in an aperiodic configuration with respect to each other. According to an example, a nanoimprinting technique or a roll-to-roll process may be implemented to form the nano-fingers 104 on the substrate 102. In this example, a template may be formed through photolithography or other advanced lithography with the desired patterning to arrange the nano-fingers 104 in the respective ordered dusters 106 and to arrange the clusters 106 into the aperiodic configuration. More particularly, for instance, the desired patterns may be designed on a mold, by E-beam lithography, photolithography, laser interference lithography, FIB (Focused on Beam), self-assembly of spheres, etc. In addition, the pattern may be transferred onto silicon, glass, or polymer substrate (PDMS, polyimide, polycarbonate, etc.). In other examples, the nano-fingers 104 may be formed in the predetermined arrangement through implementation of any suitable fabrication process.

At block 304, Raman-active material nano-particles 108 are formed on the tips of the nano-fingers 104, for instance, by deposing atoms or atom clusters 110 of the Raman-active material. The Raman-active material atoms or atom dusters 110 may be deposited onto the tips of the nano-fingers 104 through, for instance, physical vapor deposition (PVD), chemical vapor deposition (CVD), sputtering, etc., of the Raman-active material, or self-assembly of pre-synthesized nano-particles.

At block 306, the tips of the nano-fingers 104 are caused to approach each other. According to an example, the tips of the nano-fingers 104 in each of the dusters 106 are formed with a sufficiently small gap between the tips to enable the tips to move toward each other as a liquid supplied therebetween evaporates, through, for instance, capillary forces applied on the tips as the liquid dries. In various instances, the capillary forces may be sufficient to cause the tips, and the Raman-active material nano-particles 108, to contact neighboring tips and Raman-active material nano-particles 108.

According to another example, the Raman-active material nano-particles 108 may be formed on the tips of the nano-fingers 104 following the dosing of the tips in the dusters 106. In this example, blocks 304 and 306 may be reversed with respect to each other.

Figure 4:
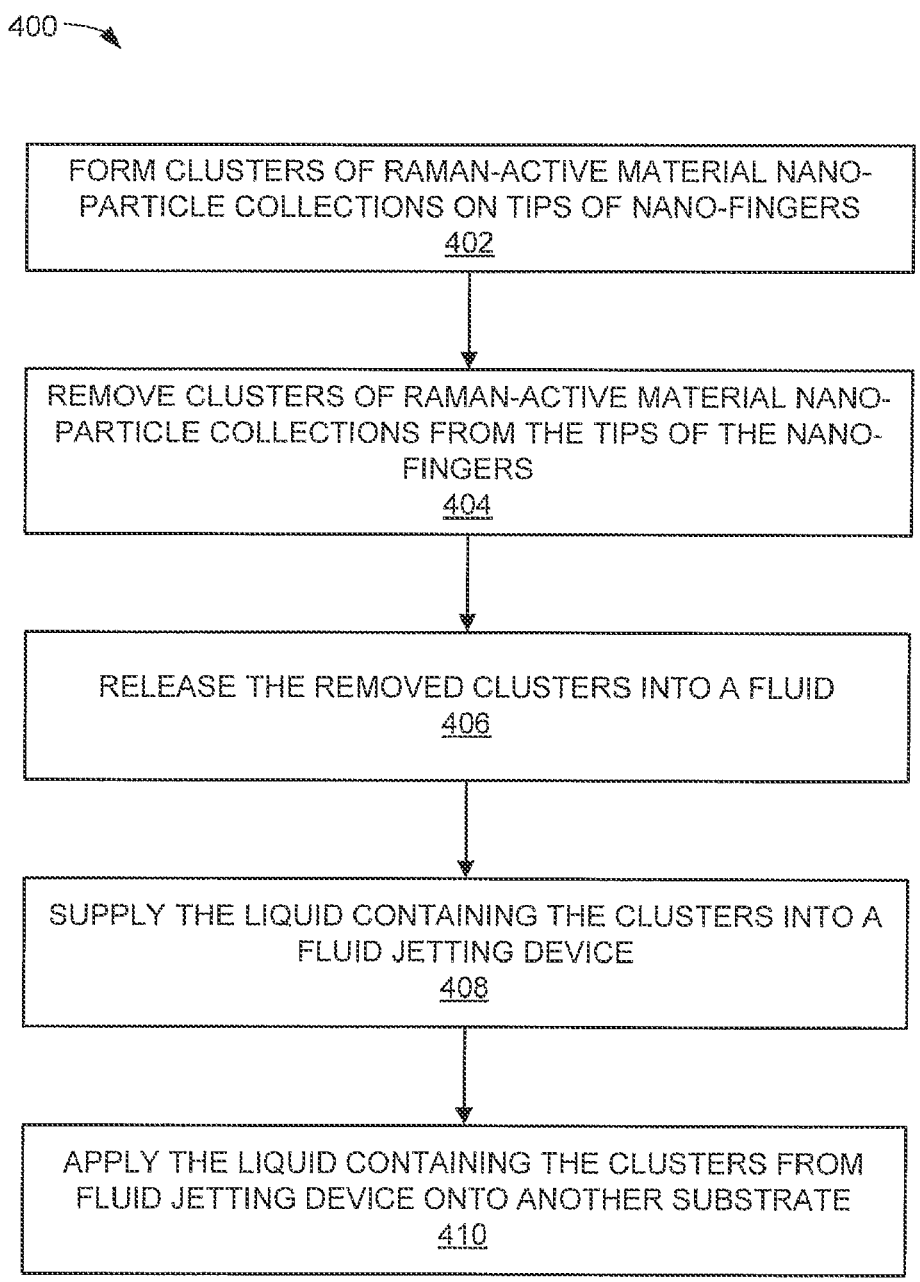

Turning now to FIG. 4, there is shown a flow diagram of a method 400 for fabricating a sensing apparatus, according to another example. It should be understood that the method 400 may include additional processes and that some of the processes described herein may be removed and/or modified without departing from a scope of the method 400. In addition, although particular reference is made herein to the apparatus 400 in implementing the method 400, it should be understood that the method 400 may be implemented through use of a differently configured apparatus without departing from a scope of the method 400.

At block 402, a plurality of clusters 106 of Raman-active material nano-particles 108 are formed on tips of a plurality of nano-fingers 104. The clusters 106 may be formed as discussed above with respect to the method 300. According to an example, the clusters 106 are formed with five Raman-active material nano-particles 108 each, in which the five Raman-active material nano-particles 108 are arranged in a pentamer configuration.

At block 404, the clusters 106 of Raman-active material nano-particles 108 are removed from the tips of the nano-fingers 104. The clusters 106 may be removed or otherwise separated from the nano-fingers 104 in any of a variety of different manners. For instance, the clusters 106 may be adhered to another substrate and lifted off of the tips. As another example, the nano-fingers 104 may be dissolved away through use of a suitable chemical agent.

At block 406, the clusters 106 are released into a fluid. In addition, at block 408, the liquid containing the clusters 106 is supplied into a fluid jetting device (not shown), such as, an inkjetting device. Moreover, at block 410, the liquid containing the clusters 106 is applied onto another substrate 232 from the fluid jetting device. According to an example, the fluid jetting device is able to apply drops of fluid containing individual clusters 106. In this example, the fluid jetting device may be employed to apply the individual clusters 106 in a desired configuration, for instance, as shown in FIGS. 1C and 1D. In addition, the clusters 106 may be deposited on substrates having a variety of different types of materials and different sizes.

Figure 5:
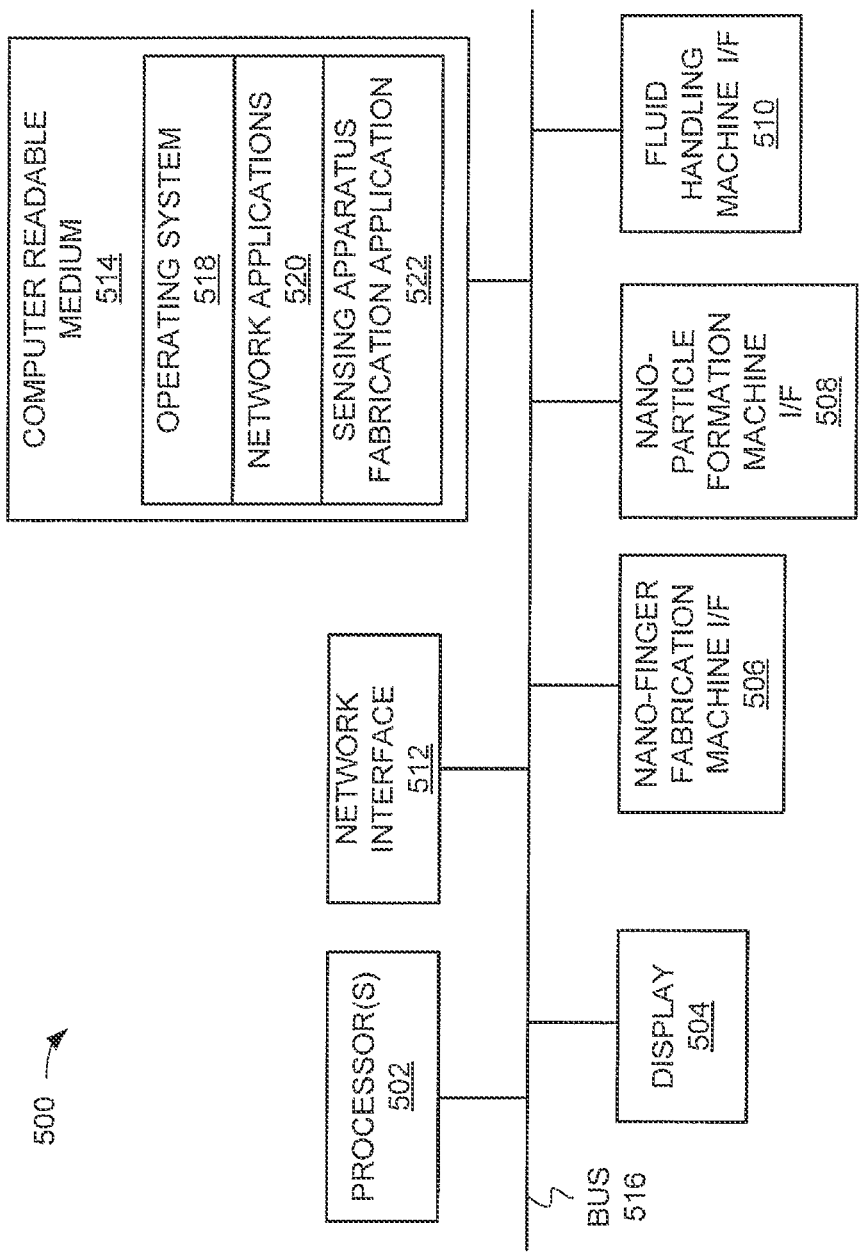
FIG. 5 shows a schematic representation of a computing device to implement or execute the methods depicted in FIGS. 3 and 4, according to an example of the present disclosure.

Turning now to FIG. 5, there is shown a schematic representation of a computing device 500 to implement or execute the methods 300, 400, according to an example. The computing device 500 includes a processor 502, such as a central processing unit; a display device 504, such as a monitor; an nano-finger fabrication machine interface 506; a nano-particle formation machine interface 508; a fluid handling machine interface 510; a network interface 512, such as a Local Area Network LAN, a wireless 802.11x LAN, a 3G mobile WAN or a WiMax WAN; and a computer-readable medium 514. Each of these components is operatively coupled to a bus 516. For example, the bus 516 may be an EISA, a PCI, a USB, a FireWire, a NuBus, or a PDS.

The nano-finger fabrication machine may comprise a machine that may be implemented to form the nano-fingers 104 as described with respect to block 302. Likewise, the nano-particle formation machine may comprise a machine that may be implemented to form the Raman-active material nano-particles 108 on to the tips of the nano-fingers 104 as described with respect to block 304. Moreover, the fluid handling machine 510 may comprise a machine that may be implemented to supply fluid onto the nano-fingers 104 that may be evaporated to cause the tips of the nano-fingers 104 in each of the clusters 106 to close upon each other.

The computer readable medium 514 may be any suitable non-transitory medium that participates in providing instructions to the processor 502 for execution. For example, the computer readable medium 514 may be non-volatile media, such as an optical or a magnetic disk; volatile media, such as memory; and transmission media, such as coaxial cables, copper wire, and fiber optics.

The computer-readable medium 510 may also store an operating system 518, such as Mac OS, MS Windows, Unix, or Linux; network applications 520; and a sensing apparatus fabrication application 522. The operating system 518 may be multi-user, multiprocessing, multitasking, multithreading, real-time and the like. The operating system 518 may also perform basic tasks such as recognizing input from input devices, such as a keyboard or a keypad; sending output to the display 504; keeping track of files and directories on the computer readable medium 510; controlling peripheral devices, such as disk drives, printers, image capture device; and managing traffic on the bus 516. The network applications 520 include various components for establishing and maintaining network connections, such as machine readable instructions for implementing communication protocols including TCP/IP, HTTP, Ethernet, USB, and FireWire.

The sensing apparatus fabrication application 522 provides various software components for implementing various machines in fabricating a sensing apparatus, as described above. In certain examples, some or all of the processes performed by the sensing apparatus fabrication application 522 may be integrated into the operating system 518. In certain examples, the processes may be at least partially implemented in digital electronic circuitry, or in computer hardware, machine readable instructions (including firmware and/or software), or in any combination thereof.

Although described specifically throughout the entirety of the instant disclosure, representative examples of the present disclosure have utility over a wide range of applications, and the above discussion is not intended and should not be construed to be limiting, but is offered as an illustrative discussion of aspects of the disclosure.

What has been described and illustrated herein is an example along with some of its variations. The terms, descriptions and figures used herein are set forth by way of illustration only and are not meant as limitations. Many variations are possible within the spirit and scope of the subject matter, which is intended to be defined by the following claims—and their equivalents—in which all terms are meant in their broadest reasonable sense unless otherwise indicated.

What is claimed is:

1. A method for fabricating a sensing apparatus, said method comprising:
    forming a plurality of nano-fingers in a predetermined arrangement, wherein the predetermined arrangement includes the plurality of nano-fingers arranged in a plurality of clusters, and wherein the plurality of clusters are arranged in an aperiodic configuration;
    forming Raman-active material nano-particles on the tips of the nano-fingers;
    causing the tips of the plurality of nano-fingers in respective ones of the clusters to approach each other to cause the Raman-active material nano-particles in each of the clusters to contact and bond with at least one other Raman-active material nano-particle in the cluster;
    removing the bonded Raman-active material nano-particles from the tips of the plurality of nano-fingers, wherein the bonded Raman-active material nano-particles retain the ordered cluster configurations; and
    applying the ordered clusters onto a substrate in the aperiodic configuration to form the sensing apparatus.

2. The method according to claim 1, wherein forming the plurality of nano-fingers further comprises:
    forming a template defining the arrangement of the plurality of nano-fingers into the ordered clusters and the clusters into the aperiodic configuration;
    transferring the template to a base; and
    implementing a fabrication process to form the plurality of nano-fingers at the defined locations on the base.

3. The method according to claim 1, wherein causing the tips of the plurality of nano-fingers in respective ones of the clusters to approach each other further comprises supplying a liquid into gaps between the tips of the plurality of nano-fingers, and wherein evaporation of the liquid causes the tips of the plurality of nano-fingers in respective ones of the clusters to approach other.

4. The method according to claim 3, further comprising:
    introducing an analyte to be tested by the sensing apparatus into the liquid to trap molecules of the analyte between at least two of the Raman-active material nano-particles as the tips of the plurality of nano-fingers approach each other.

5. The method according to claim 1, wherein forming the plurality of nano-fingers on the substrate in the predetermined arrangement further comprises forming the plurality of nano-fingers into respective pentamer clusters to cause the Raman-active material nano-particles in each of the plurality of clusters to have a pentamer configuration with respect to each other.

6. The method according to claim 1, further comprising:
    releasing the removed clusters of Raman-active material nano-particles into a fluid;
    supplying the liquid containing the clusters of Raman-active material nano-particles into a fluid jetting device; and
    wherein applying the ordered clusters further comprises jetting the ordered clusters onto the another substrate in the aperiodic configuration.

7. The method according to claim 1, wherein the removing and the applying further comprise contacting the Raman-active material nano-particles onto the substrate prior to removing the bonded Raman-active nano-particles from the tips of the plurality of nano-fingers, wherein the Raman-active material nano-particles have a stronger bond to the substrate than to the tips of the plurality of nano-fingers, and moving the substrate away from the plurality of nano-fingers to remove the bonded Raman-active material nano-particles from the tips of the plurality of nano-fingers and apply the ordered clusters onto the substrate.

8. The method according to claim 1, wherein removing the bonded Raman-active material nano-particles from the tips of the plurality of nano-fingers further comprises dissolving the plurality of nano-fingers without dissolving the bonded Raman-active material nano-particles.

* * * * *